United States Patent
Emilsson

(10) Patent No.: US 7,633,615 B2
(45) Date of Patent: Dec. 15, 2009

(54) APPARATUS FOR CAPTURING AN IMAGE

(75) Inventor: Carl-Fredrik Emilsson, Båstad (SE)

(73) Assignee: HemoCue AB, Ängelholm (SE)

( * ) Notice: Subject to any disclaimer, the term of this patent is extended or adjusted under 35 U.S.C. 154(b) by 286 days.

(21) Appl. No.: 11/717,675

(22) Filed: Mar. 14, 2007

(65) Prior Publication Data
US 2008/0018888 A1    Jan. 24, 2008

(30) Foreign Application Priority Data
Jul. 19, 2006    (SE) .................................. 0601576

(51) Int. Cl.
G01N 21/01    (2006.01)
G01N 23/00    (2006.01)

(52) U.S. Cl. .................... 356/244; 356/246; 422/64; 422/68.1; 250/492.2

(58) Field of Classification Search ............... 356/244, 356/246, 39–41, 317–319; 324/300–322; 422/63–64, 67, 100, 103, 104; 436/43, 47, 436/49, 54, 180; 360/15–17; 250/363.1, 250/287, 306–307, 492.2–492.3, 442.11
See application file for complete search history.

(56) References Cited

U.S. PATENT DOCUMENTS

| | | | |
|---|---|---|---|
| 4,479,055 A | | 10/1984 | Perten |
| 5,011,662 A | * | 4/1991 | Noormohammadi et al. ..... 422/68.1 |
| 5,306,467 A | * | 4/1994 | Douglas-Hamilton et al. .. 422/99 |
| 6,197,255 B1 | * | 3/2001 | Miyake et al. ................ 422/64 |
| 6,591,202 B1 | * | 7/2003 | Rimkunas et al. ............. 702/57 |
| 6,710,879 B1 | | 3/2004 | Hansen et al. |
| 6,852,282 B2 | * | 2/2005 | Miyake et al. ................ 422/63 |
| 6,950,253 B2 | * | 9/2005 | Wang et al. ................... 360/17 |
| 7,092,085 B1 | * | 8/2006 | DeSa ......................... 356/246 |
| 7,164,123 B2 | * | 1/2007 | Morris et al. ................ 250/287 |
| 7,321,424 B2 | * | 1/2008 | McCandless ................ 356/319 |
| 7,407,631 B2 | * | 8/2008 | Swon et al. ................. 422/104 |
| 2004/0084625 A1 | * | 5/2004 | Williams et al. ........ 250/363.03 |

FOREIGN PATENT DOCUMENTS

WO    WO2005/105277 A1    11/2005
WO    WO 2006/096126 A    9/2006

* cited by examiner

Primary Examiner—Sang Nguyen
(74) Attorney, Agent, or Firm—Buchanan Ingersoll & Rooney PC

(57) ABSTRACT

An apparatus for capturing an image of a sample retained by a sample acquiring device, comprises an image capturing unit comprising a lens arrangement with a fixed focal plane, a sample holder comprising a first magnet unit, and a second magnet unit. The sample holder is adapted to receive the sample acquiring device and is movable in relation to the lens arrangement to a first position. The sample holder is movable from the first position to a second position by means of magnetic interaction of the first magnet unit and the second magnet unit, and the image capturing unit is adapted to capture an image of the sample by means of the lens arrangement when the sample holder is in the second position.

17 Claims, 3 Drawing Sheets

APPARATUS FOR CAPTURING AN IMAGE

FIELD OF THE INVENTION

The present intention relates to an apparatus and a method for capturing an image of a sample retained by a sample acquiring device.

BACKGROUND ART

The apparatus and the method described by way of introduction are used to capture an image of a sample for analysing the sample.

PCT/SE2006/000311 (not public at filing of this application) and U.S. Pat. No. 6,710,879 disclose methods for analysing a volume of a sample by processing an image of the sample.

To capture an image of the sample, the sample is in some cases placed under a lens arrangement with either an adjustable focal plane or a lens arrangement with a fixed focal plane.

The problems with the lens arrangements with an adjustable focal plane are that they are expensive and it is difficult to adjust the focal plane of the lens arrangement to a correct position in relation to the sample.

The problems with the lens arrangements with a fixed focal plane are that the sample, for instance retained in a cuvette, has to be located in the exact same relation to the fixed focal plane of the lens arrangement each time an image is captured to obtain a reliable result.

An object of the present invention is to provide an apparatus that can capture an image of a sample retained in a sample acquiring device in a more effective way.

SUMMARY OF THE INVENTION

The present invention is new and incentive by providing an apparatus according to claim 1 and a method according to claim 15. Embodiments of the invention are described in the dependent claims.

The inventive apparatus for capturing an image of a sample retained bay a sample acquiring device, comprises an image capturing unit comprising a lens arrangement with a fixed focal plane, a sample holder comprising a first magnet unit, and a second magnet unit, the sample holder being adapted to receive the sample acquiring device and being movable in relation to the lens arrangement to a first position, in which first position the first and the second magnet unit are arranged in such close relation that they may magnetically interact, the sample holder being movable from the first position to a second position by means of magnetic interaction of the first magnet unit and the second magnet unit, and the image capturing unit being adapted to capture an image of the sample by means of the lens arrangement when the sample holder is in the second position.

This provides the advantage that the sample holder car be arranged in the second position with high accuracy and that a lens arrangement with a fixed focal point can be used to capture a reliable image of a sample.

This also provides the advantages that the number of moving mechanical parts for moving the sample holder from the first position to the second position is reduced.

By reducing the number of moving mechanical parts an advantage is obtained in that the influence of the tolerances of each part is reduced. This is particularly advantageous when the sample acquiring device provides a sample thickness equal or marginally smaller than a depth of field of the image capturing unit. In such cases, a slight malpositioning of the sample acquiring device would render analysis of the captured image impossible or, worse, would render incorrect results of the analysis.

A further advantage is that by moving the sample holder by means of magnetic interaction, the wear of the apparatus is reduced.

To introduce a sample acquiring device in an easy and reliable way the apparatus can further comprise an inlet station, the sample holder being adapted to receive said sample acquiring device in said inlet station.

To achieve the advantages of positioning the sample holder in a reliable, easy and exact position the apparatus can further comprise a third magnet unit, the third magnet unit being adapted to position the sample holder in the inlet station by means of magnetic interaction of the first magnet unit and the third magnet unit. A further advantage is that the sample holder is easy to remove from the apparatus for cleaning.

The apparatus can further comprise a transfer unit, the transfer unit being arranged to support the sample holder and to transfer said sample holder from the inlet station to the first position. This leads to the advantages that the sample holder can be transferred in an easy, reliable and correct way.

The transfer unit of the apparatus can be movable between the inlet station and a position in which the sample holder is positioned in the first position.

To achieve the advantages of increasing the reliability of the apparatus, the second magnet unit of the apparatus can be arranged on the transfer unit.

To increase the reliability of the apparatus and to support the sample holder when it is moved from the inlet station to the first position the third magnet unit of the apparatus can be arranged on the transfer unit.

To reduce the tolerance with which the sample holder is positioned in the second position the apparatus can further comprise an alignment means for aligning the sample holder in relation to the lens arrangement when it is moved from the first to the second position.

The alignment means of the apparatus can be arranged on the transfer unit.

The first and the second magnet unit of the apparatus can be arranged to move the sample holder from the first position to the second position by means of repellent magnetic forces. This leads to the advantages that the sample holder is arranged in the second position with a very high tolerance.

To achieve the advantages of the sample holder being maintained in an correct position when it is moved the first and the third magnet unit of the apparatus can be arranged to position the sample holder in the inlet station by means of attracting magnetic forces.

The sample holder of the apparatus can be adapted to receive a sample acquiring device in the form of a cuvette.

The apparatus can further comprise an image processing unit, the image processing unit being adapted to process an image of the sample.

The image processing unit of the apparatus can be adapted to identify and count particles in the sample. In particular, the image processing unit malt be adapted to identify and count biological particles, such as blood cells, in a liquid sample, such as blood.

The inventive method for capturing an image of a sample retained by a sample acquiring device, comprises: positioning the sample acquiring device in a sample holder comprising a first magnet unit, transferring said sample holder in relation to a lens arrangement with a fixed focal plane of an image capturing unit to a first position, in which first position the first and a second magnet unit are arranged in such close relation that they may magnetically interact, moving the sample holder from the first position to a second position by means of magnetic interaction of the first magnet unit and the second magnet unit, and capture an image of the sample by means of the lens arrangement when the sample holder is in the second position.

Advantages of she inventive method are that an image of a sample can be captured in a reliable and easy way.

The method can further comprise processing said image in an image processing unit and to identify and count particles in the sample.

BRIEF DESCRIPTION OF THE DRAWINGS

The invention and its many advantages will be described in more detail below with reference to the accompanying schematic drawings, which for the purpose of illustration show some non-limiting embodiments and in which.

All figures are highly schematic, not necessarily to scale, and they show only parts, which are necessary in order to elucidate the invention, other parts being omitted or merely suggested.

DESCRIPTION OF PREFERRED EMBODIMENTS

Figure 1:
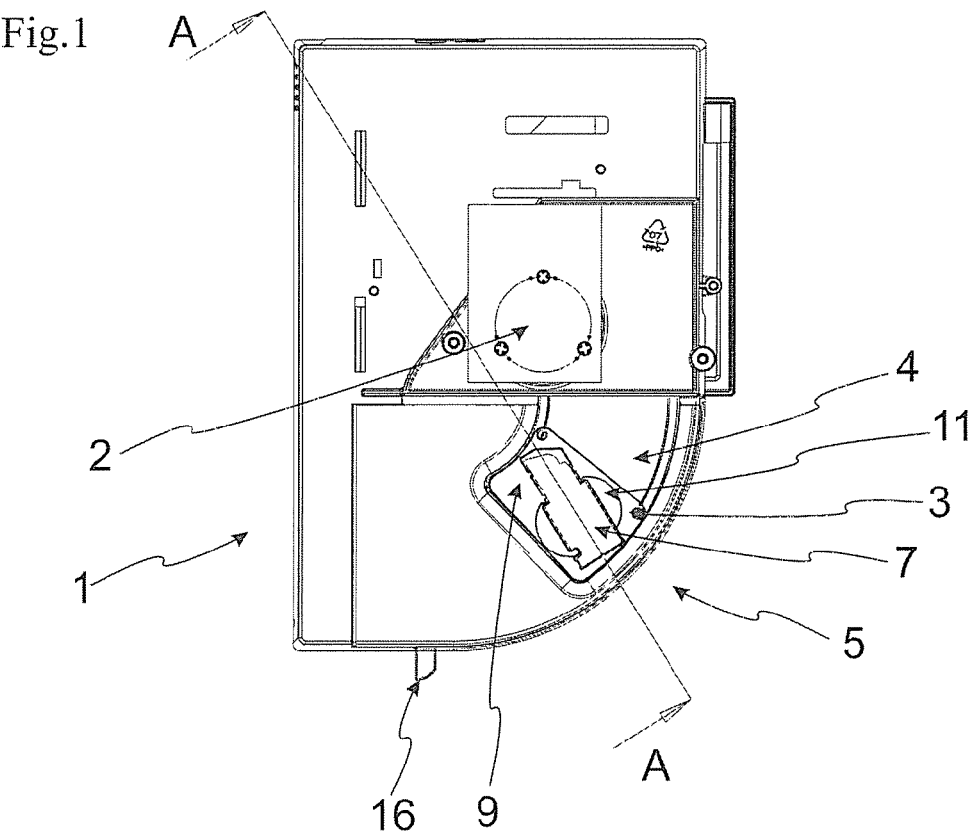
FIG. 1 shows a plan view of an embodiment of the invention when the sample holder is arranged in the inlet station.
Figure 2:
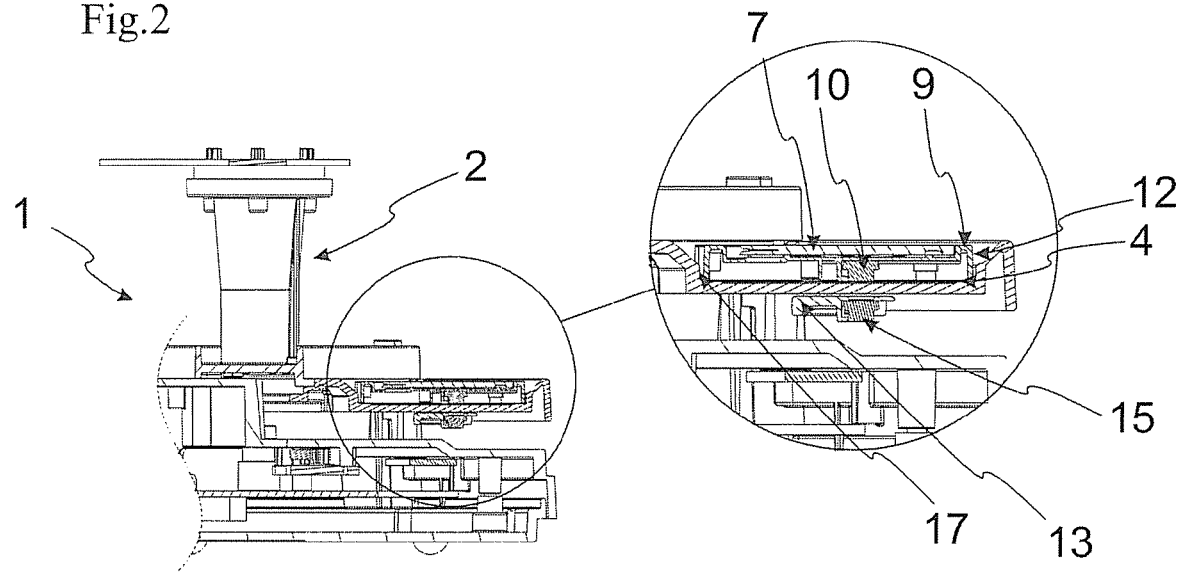
FIG. 2 shows a partial cross-sectional view of the embodiment in FIG. 1 along A-A.

FIGS. 1 and 2 show an embodiment of an apparatus according to the invention. The apparatus 1 comprises an image capturing unit 2, a sample holder 3, a transfer unit 4 and an inlet station 5. In the shown embodiment, the sample holder 3 has received a sample acquiring device 7, in the form of a cuvette 7.

The image capturing unit 2 comprises a lens arrangement 6 with a fixed focal plane. In the shown embodiment the lens arrangement 6 comprises four lenses 8, see FIG. 4.

The sample holder 3 comprises a plate 9 and a first magnet unit 10. The plate 9 comprises a central depression 11 on an upper side and a flange 12 that is arranged on the circumference of a lower side of the plate 9 and that extends in a direction away from the upper side. The first magnet unit 10 is mounted on the lower side of the plate 9. The central depression 11 has a shape that corresponds to the shape of the sample acquiring device 7.

The transfer unit 4 comprises a support plate 13, a second magnet unit 14, a third magnet unit 15 and a handle 16. The support plate 13 is curved in the direction of its length. The support plate 13 comprises a depression 17 on the upper side, the shape of the depression 17 corresponds to the shape of the sample holder 3. The second magnet unit 14 and the third magnet unit 15 are mounted on the lower side of the support plate 13. The handle 16 is mounted on the side of the support plate 13, which has the largest radius. The support plate 13 of the transfer unit 4 is movable by movement of the handle 16.

The sample holder 4 is arranged in the depression 17 of the support plate 13. As the support plate 13 of the transfer unit 4 is moved by turning the handle 16 the sample holder 3 moves together with support plate 13 of the transfer unit 4. The handle 16 of the transfer unit 4 is arranged to move the sample holder 3 between the inlet station 5 and a first position 18.

The first and third magnet unit 10, 15 are magnets being arranged with attracting magnetic poles facing each other. The first and the second magnet units 10, 14 are magnets being arranged with repellent magnetic poles facing each other. The third magnet unit 15 is mounted on the support plate 13 in a position such that, when the sample holder 3 is arranged in the inlet station 5, the first and the third magnet unit 10, 15 interacts and presses the sample holder 3 against the support plate 13. To move the sample holder 3 to the first position the handle 16 of the transfer unit 4 first is turned 75 degrees, and thereby also moving the sample holder 3. After being turned 75 degrees the sample holder 3 hits an abutment (not shown). The handle 16 of transfer unit 4 is thereafter turned another 15 degrees. By doing this the support plate 13 of the transfer unit 4 is moved in relation to the sample holder 3, such that the second magnet unit 14 is aligned with the first magnet unit 10. The sample holder 3 is now in its first position 18.

Figure 3:
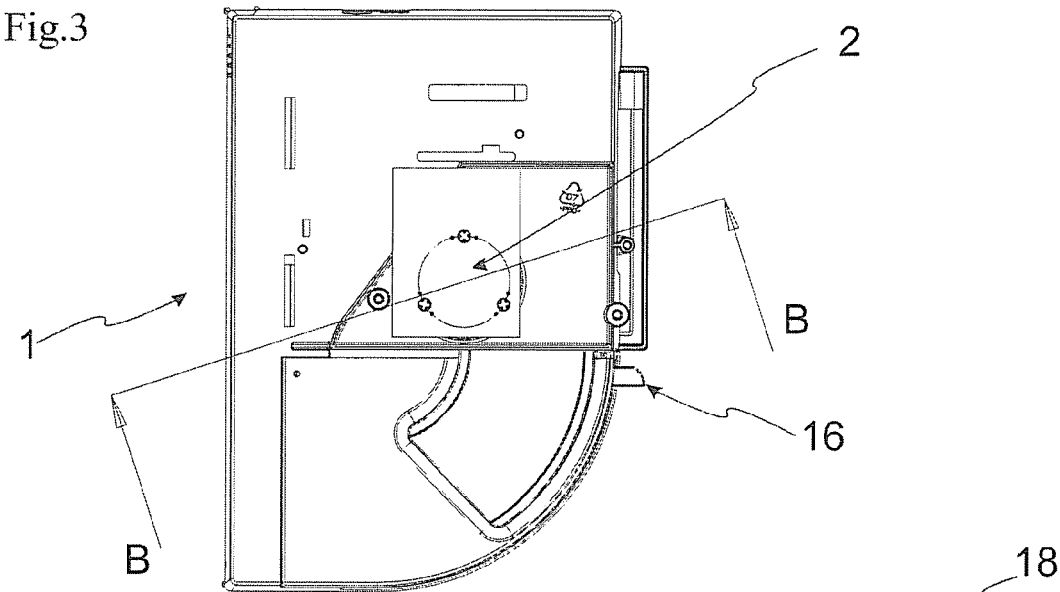
FIG. 3 shows a plan view of an embodiment of the invention when the sample holder is arranged in the second position.
Figure 4:
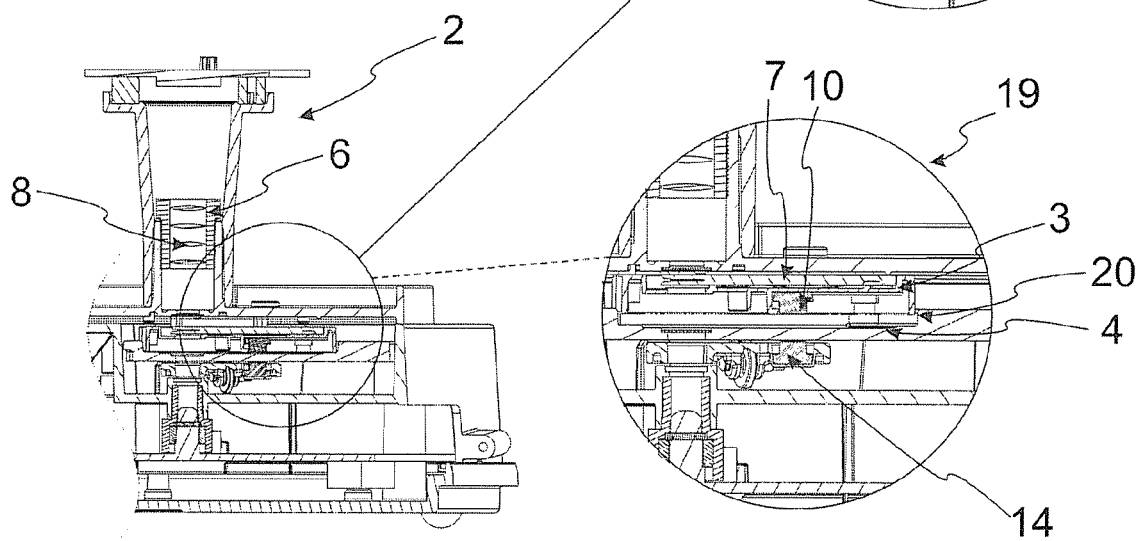
FIG. 4 shows a partial cross-sectional view of the embodiment in FIG. 3 along B-B.

To move the sample holder 3 to a second position 19 the first and the second magnet unit 10, 14 interact, see FIGS. 3 and 4. As the first and second magnet units 10, 14 are arranged with repellent magnetic poles facing each other, the sample holder 3 will be moved upwards. The flanges 12 and an alignment means 20 of the support plate 13 interact when the sample holder 3 is moved upwards to guide the movement of and align the sample holder 3 with an optical axis of the lens arrangement 6. The alignment means 20 can be constituted of the walls 20 of the depression 17. As the sample holder 3 has moved a distance from the support plate 13 of the transfer unit 4, there will be equilibrium between the magnetic forces interacting between the first and second magnetic unit 10, 14 and the weight of the sample holder 3, the sample acquiring device 7 and the sample. The sample holder 3 is now in its second position 19.

The second position 19 can also be constituted of that the magnetic interaction of the first and the second magnet units 10, 14 presses the sample holder 3 against a second abutment.

The second position 19 is a position in the apparatus 1 in which the sample in the sample acquiring device 7 is located at a predetermined distance from the lens arrangement 6 of the image capturing unit 2. This predetermined distance is calibrated so that the fixed focal plane of the lens arrangement 6 correlates to the position of sample such that the image capturing unit 2 can capture a desired image.

To remove the cuvette 7 from the apparatus 7, the handle 16 of the transfer unit 4 is turned 15-degrees in the opposite direction. After turning, the third magnet unit 15 will be arranged in such a close relation with the first magnet unit 10 that they may magnetically interact. Interaction by means or attracting magnetic forces will more the sample holder 3 and press it against the support plate 13 of the transfer unit 4. Thereafter the handle 16 is turned another 75 degrees and thereby the sample holder 3 is transferred back to the inlet station 5.

When an image of a sample is to be captured, a volume of the sample, for instance a blood sample, is acquired in a cuvette 7. The volume of the sample can be relatively large, i.e. the volume of the sample allows particles therein to be located in a 3-dimensional relation to each other. For instance, the sample may be acquired into a measurement cavity having a thickness of 140 μm.

The transfer unit 4 and the sample holder 3 are arranged in the inlet station 5. The first and the third magnet unit 10, 15 interact and keep the sample holder 3 stabile. The cuvette 7 is arranged in the inlet station 5 and the sample holder 3 receives it.

The handle 16 of the transfer unit 4 is turned 90 degrees. As support plate 13 of the transfer unit 4 is moved, the sample holder 3 is moved to the first position 18.

In the first position 18 the first and the second magnet units 10, 14 interact and the sample holder 3, and thus also the cuvette 7 and the sample retained by the cuvette 7, is moved to the second position 19.

In the second position 19 the sample is located at a predetermined distance from the lens arrangement 6 of the image capturing unit 2, in which the fixed focal plane of the lens arrangement 6 correlates with the sample in a desired way. The measurement cavity of the cuvette 7 is thus placed such that the entire thickness of the measurement cavity is within the field of image capturing unit 2.

The image capturing unit 2 thereafter captures an image of the sample via the lens arrangement 6. Thereafter the image can be forwarded from the image capturing unit 2 to a computer or an image processing unit.

Figure 5:
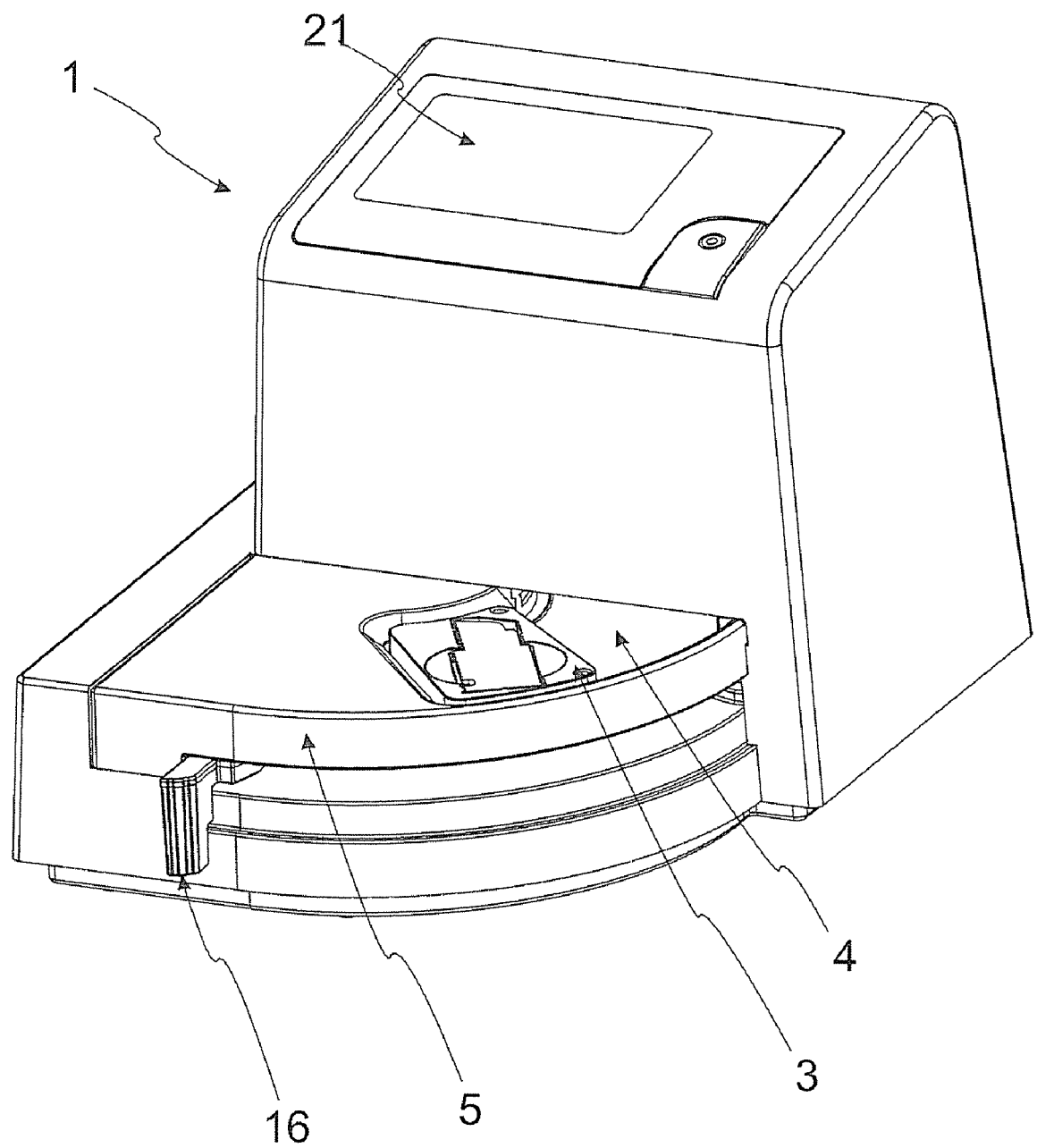
FIG. 5 shows a perspective view of a second embodiment of the invention

In a second embodiment of the invention the apparatus further comprises an image processing unit (not shown), see FIG. 5. The image capturing unit 2 forwards the image captured of the sample to the image processing unit. The image processing unit then analyzes the image of the sample, for instance it can be used to count the number of white blood cells in a blood sample, and display the result on a display 21.

The sample holder 3 is held in place in the inlet station 2 by magnetic interaction of the first and the third magnet unit 10, 15, the sample holder 3 is thus easy to remove from the apparatus 1. A user could grasp the sample holder 3 and remove it by applying a pulling force that exceeds the magnetic force between the first and the third magnet units 10, 15. If some part of the sample leaks from the sample acquiring device 7 it will be collected in the sample holder 3. It is thus an advantage that the sample holder 3 is easy to clean. If the sample holder 3 is contaminated with remains from an old sample, the image of the sample could be incorrect.

Although the invention above has been described in connection with preferred embodiments of the invention, it will be evident for a person skilled in the art that several modification are conceivable without departing from the invention as defined by the following claim.

The invention claimed is:

1. Apparatus for capturing an image of a sample retained by a sample acquiring device, comprising an image capturing unit comprising a lens arrangement with a fixed focal plane, a sample holder comprising a first magnet unit, and a second magnet unit,
   the sample holder being adapted to receive the sample acquiring device and being movable in relation to the lens arrangement to an aligned position, in which aligned position the first and the second magnet units are arranged in such close relation that they may magnetically interact,
   the sample holder being movable upwards in relation to the apparatus from the aligned position to an interaction position by magnetic interaction of the first magnet unit and the second magnet unit, and
   the image capturing unit being adapted to capture an image of the sample by the lens arrangement when the sample holder is in the interaction position.

2. Apparatus according to claim 1, further comprising an inlet station, the sample holder being adapted to receive said sample acquiring device in said inlet station.

3. Apparatus according to claim 2, further comprising a third magnet unit,
   the third magnet unit being adapted to position the sample holder in the inlet station by magnetic interaction of the first magnet unit and the third magnet unit.

4. Apparatus according to claim 3, wherein the first and third magnet units are arranged to position the sample holder in the inlet station by attracting magnetic forces.

5. Apparatus according to claim 2, further comprising a transfer unit,
   the transfer unit being arranged to support the sample holder and to transfer said sample holder from the inlet station to the aligned position.

6. Apparatus according to claim 5, wherein the transfer unit is movable between the inlet station and a position in which the sample holder is positioned in the aligned position.

7. Apparatus according to claim 5, wherein the second magnet unit is arranged on the transfer unit.

8. Apparatus according to claim 5, wherein the third magnet unit is arranged on the transfer unit.

9. Apparatus according to claim 1, further comprising an alignment means for aligning the sample holder in relation to the lens arrangement when it is moved from the first to the interaction position.

10. Apparatus according to claim 9, wherein the alignment means is arranged on the transfer unit.

11. Apparatus according to claim 1, wherein the first and the second magnet units are arranged to move the sample holder from the aligned position to the interaction position by repellent magnetic forces.

12. Apparatus according to claim 1, wherein the sample holder is adapted to receive a sample acquiring device in the form of a cuvette.

13. Apparatus according to claim 12, wherein the cuvette is placed horizontally in the sample holder for image capturing.

14. Apparatus according to claim 1, further comprising an image processing unit,
   the image processing unit being adapted to process an image of the sample.

15. Apparatus according to claim 14, wherein the image processing unit is adapted to identify and count particles in the sample.

16. Method for capturing an image of a sample in a sample acquiring device, said method comprising:
   positioning the sample acquiring device in a sample holder comprising a first magnet unit,
   transferring said sample holder in relation to a lens arrangement with a fixed focal plane of an image capturing unit to an aligned position, in which aligned position the first and a second magnet units are arranged in such close relation that they may magnetically interact,
   moving the sample holder upwards in relation to the apparatus from the aligned position to an interaction position by magnetic interaction of the first magnet unit and the second magnet unit, and
   capturing an image of the sample by the lens arrangement when the sample holder is in the interaction position.

17. Method according to claim 16, further comprising:
   processing said image in an image processing unit in order to identify and count particles in the sample.

* * * * *